United States Patent
Kim et al.

(10) Patent No.: US 11,612,411 B2
(45) Date of Patent: Mar. 28, 2023

(54) APPARATUS FOR AUTOMATICALLY SEPARATING HAIR FOLLICLES

(71) Applicants: Tae Hee Kim, Seoul (KR); Kyoung Ku Lee, Seoul (KR)

(72) Inventors: Tae Hee Kim, Seoul (KR); Kyoung Ku Lee, Seoul (KR)

( * ) Notice: Subject to any disclaimer, the term of this patent is extended or adjusted under 35 U.S.C. 154(b) by 617 days.

(21) Appl. No.: 16/564,269

(22) Filed: Sep. 9, 2019

(65) Prior Publication Data

US 2020/0000964 A1    Jan. 2, 2020

Related U.S. Application Data

(63) Continuation of application No. PCT/KR2018/008642, filed on Jul. 30, 2018.

(30) Foreign Application Priority Data

Aug. 9, 2017   (KR) .................... 10-2017-0101058

(51) Int. Cl.
| | |
|---|---|
| *A61B 17/322* | (2006.01) |
| *A61B 17/00* | (2006.01) |
| *A61L 27/36* | (2006.01) |
| *A61F 2/10* | (2006.01) |

(52) U.S. Cl.
CPC ............... *A61B 17/322* (2013.01); *A61F 2/10* (2013.01); *A61L 27/3604* (2013.01); *A61L 27/3691* (2013.01); *A61B 2017/00752* (2013.01); *A61F 2240/00* (2013.01)

(58) Field of Classification Search
CPC ........ A61B 17/322; A61B 2017/00752; A61B 2017/3225
See application file for complete search history.

(56) References Cited

U.S. PATENT DOCUMENTS

| | | | | |
|---|---|---|---|---|
| 4,768,517 | A | * | 9/1988 | Joachim ............... A61B 18/203 606/187 |
| 5,782,843 | A | * | 7/1998 | Aasberg .................... A61F 2/10 606/187 |
| 5,895,403 | A | | 4/1999 | Collisworth |

(Continued)

FOREIGN PATENT DOCUMENTS

| | | |
|---|---|---|
| KR | 10-2010-0003360 A | 1/2010 |
| KR | 10-0939134 B1 | 1/2010 |

(Continued)

OTHER PUBLICATIONS

International Search Report dated Nov. 2, 2018 for corresponding the international application No. PCT/KR2018/008642.

*Primary Examiner* — Sarah A Simpson
*Assistant Examiner* — Raihan R Khandker
(74) *Attorney, Agent, or Firm* — Hauptman Ham, LLP

(57) ABSTRACT

An apparatus for automatically separating hair follicles includes a follicle separating unit configured to cut a skin tissue of a scalp cut from a back of a head of an alopecic patient in units of follicles and to classify follicles by a number of hairs included in each follicle in an incisional hair transplant or to classify follicles each directly extracted from the back of the head of the alopecic patient by the number of hairs included in each follicle in a non-incisional hair transplant, and a follicle separation control unit configured to control an operation of the follicle separating unit.

7 Claims, 18 Drawing Sheets

(56) References Cited

U.S. PATENT DOCUMENTS

| | | | | |
|---|---|---|---|---|
| 2009/0088720 | A1* | 4/2009 | Oostman, Jr. | A61F 2/10 |
| | | | | 606/130 |
| 2016/0193035 | A1* | 7/2016 | Silva Ramos | A61F 2/10 |
| | | | | 606/130 |
| 2017/0020566 | A1* | 1/2017 | Bae | A61B 17/32053 |
| 2018/0360527 | A1* | 12/2018 | Boinagrov | A61B 34/30 |

FOREIGN PATENT DOCUMENTS

| | | |
|---|---|---|
| KR | 10-1030853 B1 | 4/2011 |
| KR | 10-2015-0014013 A | 2/2015 |

\* cited by examiner

APPARATUS FOR AUTOMATICALLY SEPARATING HAIR FOLLICLES

CROSS-REFERENCE TO RELATED APPLICATIONS

This application is a continuation of International Application No. PCT-KR2018-008642, filed Jul. 30, 2018, which is based upon and claims the benefit of priority from Korean Patent Application No. 10-2017-0101058, filed on Aug. 9, 2017, the contents of which are incorporated herein by reference in their entirety.

BACKGROUND

1. Field

The present invention relates to an apparatus for automatically separating hair follicles.

2. Description of the Related Art

As the human body ages, hair loss (alopecia) may be experienced, wherein hair falls out from the scalp, for various reasons such as physical changes, genetic effects, hormone effects, eating habits, stress, irregular lifestyles, and environmental factors. Alopecia patients account for about 20% to 30% of the world's population, and the percentage continues to increase.

Especially in modern society where great importance is attached to beauty, the quantity of hair has a lot of influence on appearance. In general, when hair loss occurs, self-confidence decreases and may be the cause of stress such as appearing older than the person's age. Thus, according to the stage of hair loss, various types of hair loss management methods have been proposed, such as scalp management, hair loss shampoo, drug treatment, and self-hair transplants.

In self-hair transplants, since follicles without hair loss genes are taken from the back of the head, hair loss is permanently prevented and the effect is visible to the naked eye within a short period of time. Recently, hair transplants for young people have also been on the rise for beauty purposes, to look younger and boost self-confidence or to organize the forehead hairline. Such self-hair transplants can be divided into an incisional hair transplant method that removes a portion of the patient's own scalp and a non-incisional hair transplant method that extracts only follicles one by one.

In the conventional method of incisional hair transplants, several follicle separating professionals separate the follicles one by one after cutting and removing a portion of the scalp, which takes a long time and the speed of separating hair follicles varies greatly depending on the skill of the worker. In addition, there are problems such as irregular separation of follicles, varying quality of follicle separation even if a same worker does the job depending on the worker's condition that day, long operation time which makes the patient feels uncomfortable and increases operation costs due to the labor costs of the follicle separating professional.

In addition, in the conventional method of non-incisional hair transplants, follicles are extracted and then the connective tissue of the extracted follicles need cutting and trimming so that they can be easily planted on the scalp. Accordingly, there are problems where the fatigue level of both doctor and patient increases, and as the concentration of the doctor decreases due to the accumulation of fatigue, this causes damage to healthy follicles such as cutting the same when collecting the follicles, which lowers engraftment rate.

SUMMARY

An apparatus for automatically separating hair follicles according to some embodiments of the present invention includes a follicle separating unit configured to cut a skin tissue of a scalp cut from a back of a head of an alopecic patient in units of follicles and to classify follicles by a number of hairs included in each follicle in an incisional hair transplant or to classify follicles each directly extracted from the back of the head of the alopecic patient by the number of hairs included in each follicle in a non-incisional hair transplant, and a follicle separation control unit configured to control an operation of the follicle separating unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
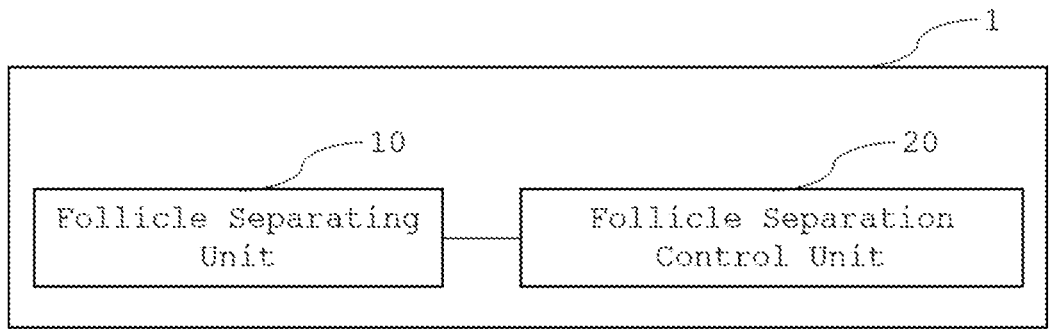
FIG. 1 is a functional block diagram of an automatic hair-follicle separating apparatus according to some embodiments of the present invention.

Exemplary embodiments of the present disclosure are described in detail below with reference to the accompanying drawings. In the following descriptions, like reference numerals designate like elements although the elements are shown in different drawings. Further, detailed descriptions of known functions and configurations incorporated herein are omitted for the purpose of clarity and for brevity.

The present invention is directed to providing an automatic hair-follicle separating apparatus configured such that when classifying follicles by a number of hairs included in each follicle by separating the follicles from a skin tissue cut out from a certain part of a scalp of an alopecic patient in an incisional hair transplant, or classifying follicles by a number of hairs included in each follicle directly extracted from the back of the head of the alopecic patient in a non-incisional hair transplant, it is possible to minimize the loss of healthy follicles regardless of the skill and fatigue level of a worker, to automatically make selections depending on the number of hairs formed in each separated follicle to save operation time and thereby relieving the physical stress on doctors and patients, to separate the follicles at a high speed so that the follicles are quickly delivered in an undried state to increase the engraftment rate of transplanted hair, and to automatically separate follicles without the need for follicle separating professionals to reduce labor costs and thereby ultimately reducing the cost of surgery for patients to generalize hair transplant surgeries.

In the present specification, a skin tissue refers to a tissue cut out from a certain part of a back of a head of an alopecic patient where there are no hair loss genes.

In the present specification, a connective tissue refers to a tissue surrounding and supporting units of follicles in the skin tissue.

FIG. 1 is a functional block diagram of an automatic hair-follicle separating apparatus 1 according to some embodiments of the present invention. As shown in FIG. 1, the automatic hair-follicle separating apparatus 1 includes a follicle separating unit 10 and a follicle separation control unit 20.

The follicle separating unit 10 collects various information and data on an image obtained by scanning the scalp cut from a back of a head of an alopecic patient, and after separating units of follicles from a connective tissue without damaging the same, follicles are selected and stored based on the number of hairs formed in each of the separated units of follicles.

Figure 2:
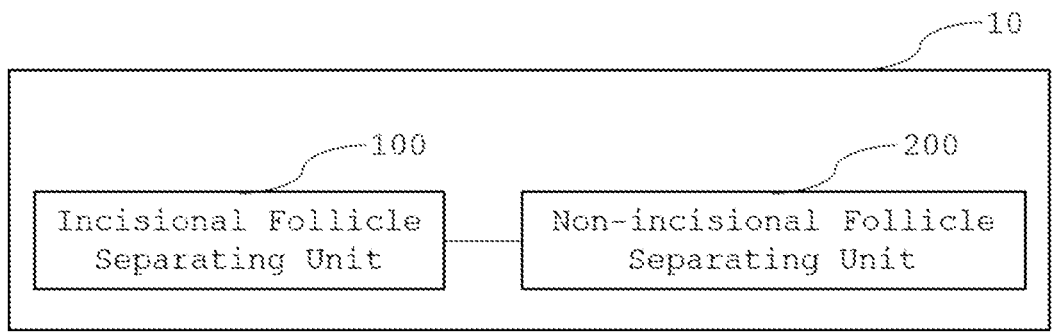
FIG. 2 is a functional block diagram of a follicle separating unit according to some embodiments of the present invention.

As shown in FIG. 2, the follicle separating unit 10 includes an incisional follicle separating unit 100 and a non-incisional follicle separating unit 200.

Figure 3:
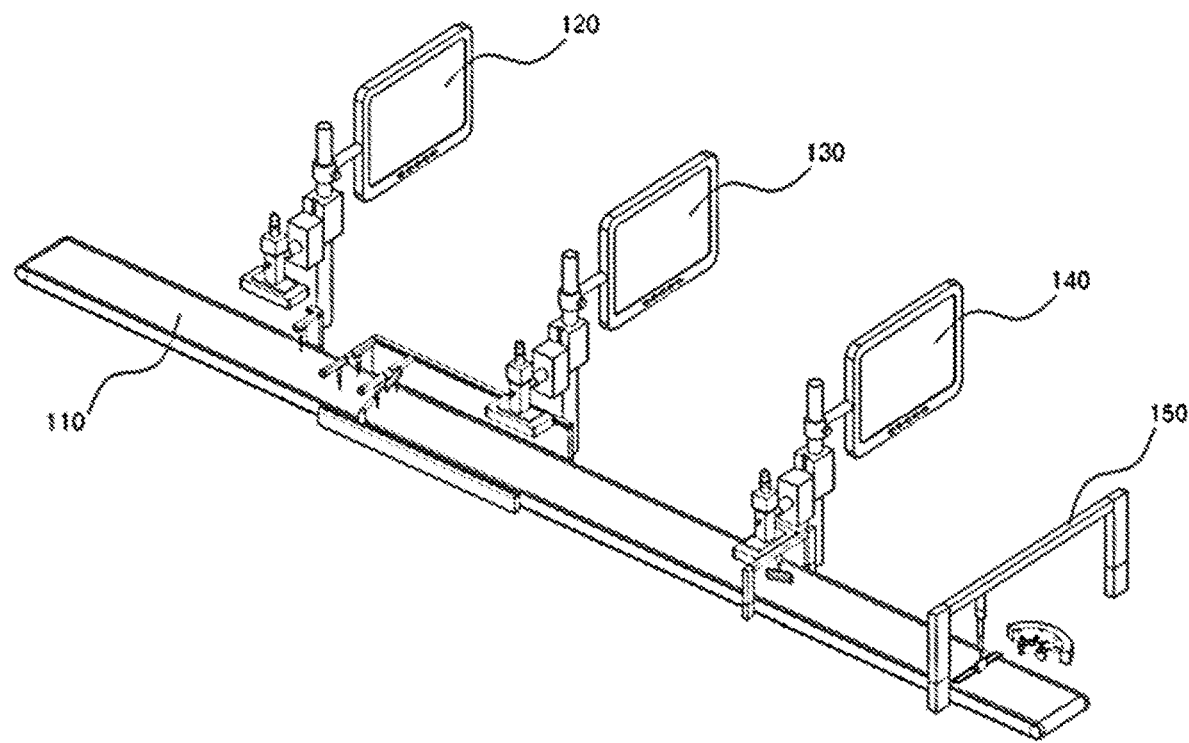
FIG. 3 is a perspective view of the automatic hair-follicle separating apparatus according to some embodiments of the present invention.

The incisional follicle separating unit 100 is configured to scan the scalp cut from the back of the head of the alopecic patient to separate each unit of follicles from the connective tissue formed in the skin tissue, and to select follicles based on the number of hairs included in a unit of follicles. As shown in FIG. 3, the incisional follicle separating unit 100 includes a conveyor belt (a transporting unit 110), a scalp data analyzing unit 120, a first cutting unit 130, a second cutting unit 140 and a follicle selective unit 150.

The conveyor belt 110 is a conveyor belt formed horizontally from a leading end to a trailing end and configured to rotate in a single linear direction by a rotation of a driving motor controlled by the follicle separation control unit 20 to transport the connective tissue including a unit of follicles positioned on one side above the conveyor belt 110.

The conveyor belt 110 is configured to have a locking projection formed protruding to the left and right peripheral ends of a belt rail such that an antibacterial cutting plate 111 (see FIG. 14) is fitted and coupled along the central periphery.

The antibacterial cutting plate 111 directly supports the skin tissue including the follicles and transports the skin tissue according to the rotation of the conveyor belt 110.

Figure 14:
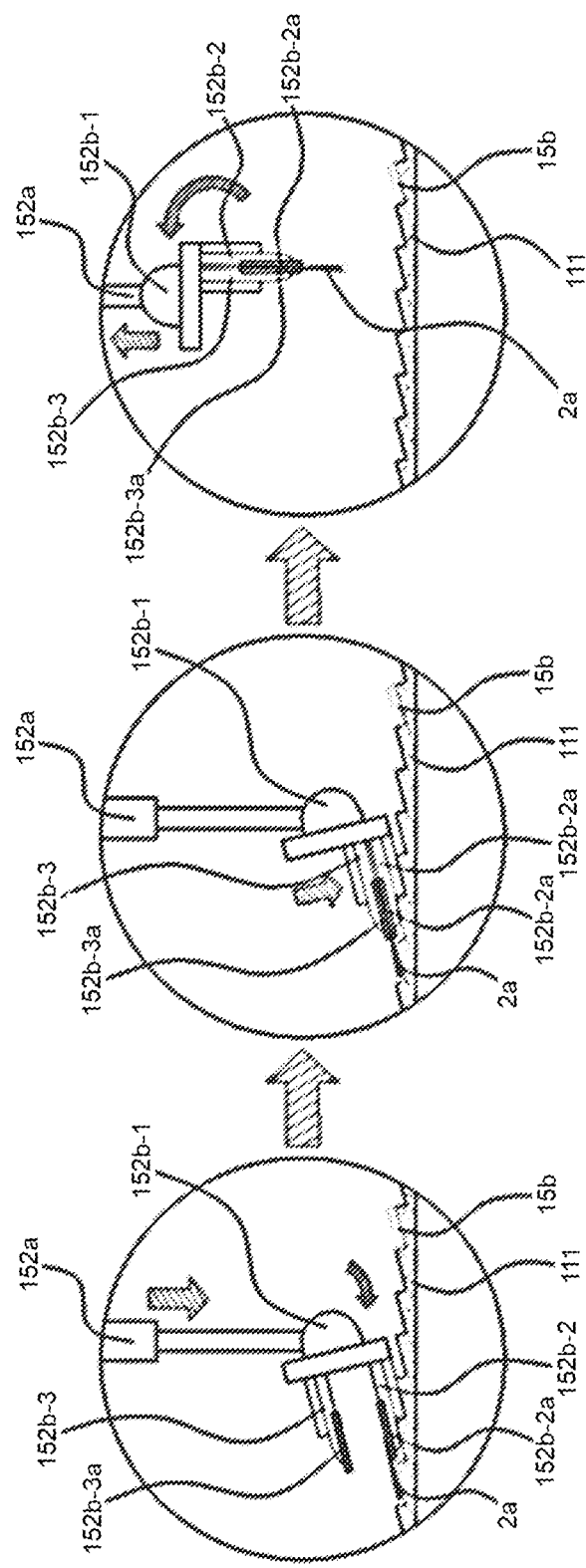
FIG. 14 is a schematic diagram showing an operation procedure of a selective follicle transporting unit according to some embodiments of the present invention.

As shown in FIG. 14, the antibacterial cutting plate 111 is sterilized by a belt having a repetitive sawtooth shape pattern with a slope heading upward in a forward direction and formed of an antibacterial, corrosion-resistant and elastic material (for example, silicon).

The antibacterial cutting plate 111 prevents contamination and damage of follicles by blocking infection caused by exposure to bacteria through the side of the connective tissue in direct contact cut from a patient.

According to some embodiments of the present invention, the antibacterial cutting plate 111 is composed of disposable consumables that are discarded when follicle separation is completed in consideration of hygiene issues.

The scalp data analyzing unit 120 scans the cut skin tissue to measure the average density of hairs formed in the scalp, measures the hardness of the skin tissue, and collects dataficated information.

Figure 4:
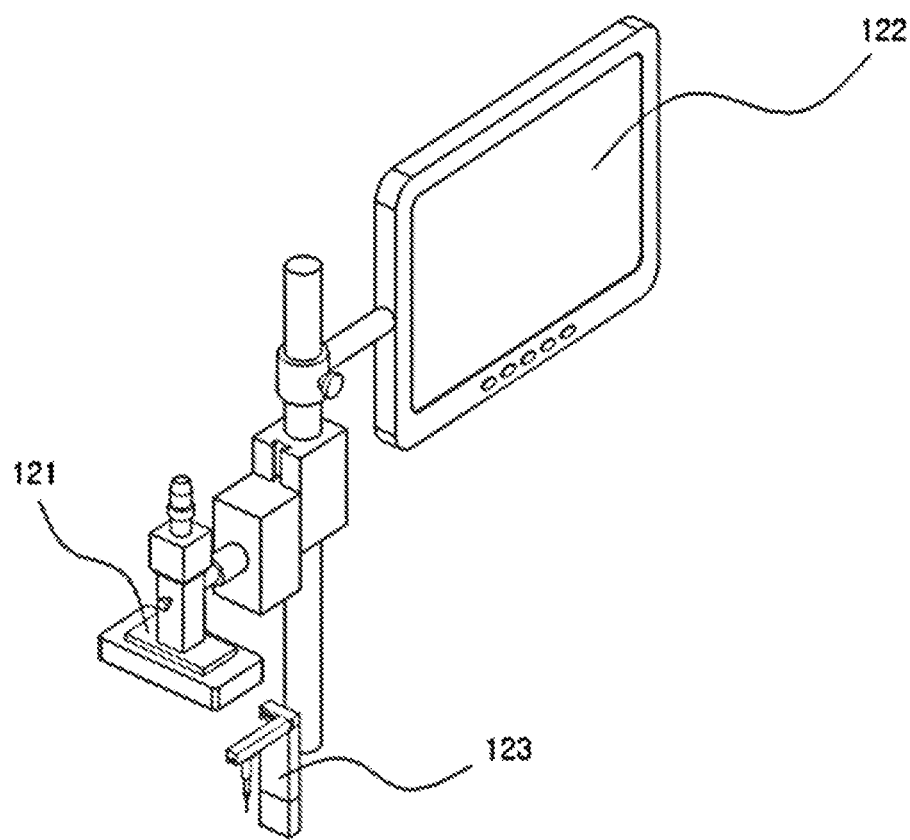
FIG. 4 is a perspective view of a scalp data analyzing unit according to some embodiments of the present invention.

As shown in FIG. 4, the scalp data analyzing unit 120 includes a scanning unit 121, a monitor unit 122, and a skin hardness measuring unit 123.

The scanning unit 121 is positioned in the vertical direction on an upper side of a conveyor belt unit, and is configured to include moving up and down along a scanning guide rail formed in an up-and-down direction, scanning a cut skin tissue as a whole to determine a follicle distribution, and measuring an interval between follicles to determine an average density of the hair in the skin tissue.

According to some embodiments of the present invention, the scanning unit 121 scans the whole skin tissue by moving up and down in an up-and-down direction according to the size and length of the cut skin tissue and adjusting the focal length, and it is possible to zoom in/out of the portion to be scanned to provide the monitor unit 122 with a partially enlarged and reduced screen.

The monitor unit 122 enlarges and displays the screen scanned by the scanning unit 121, and outputs the information measured by the skin hardness measuring unit 123 to the screen.

That is, the monitor unit 122 allows a doctor to visually check the overall state of the cut skin tissue, and provides information on the skin hardness measured by the skin hardness measuring unit 123.

According to some embodiments of the present invention, the skin hardness measuring unit 123 is positioned to be supported by one side of the left side of the conveyor belt, a skin hardness measuring pin moves in x and y directions in the upper direction of the conveyor belt, and when a skin tissue is detected by a skin tissue sensor for the first time, it is lowered vertically and the skin hardness measuring pin positioned at a lower end measures the intensity of the force piercing through the scalp tissue.

Figure 5:
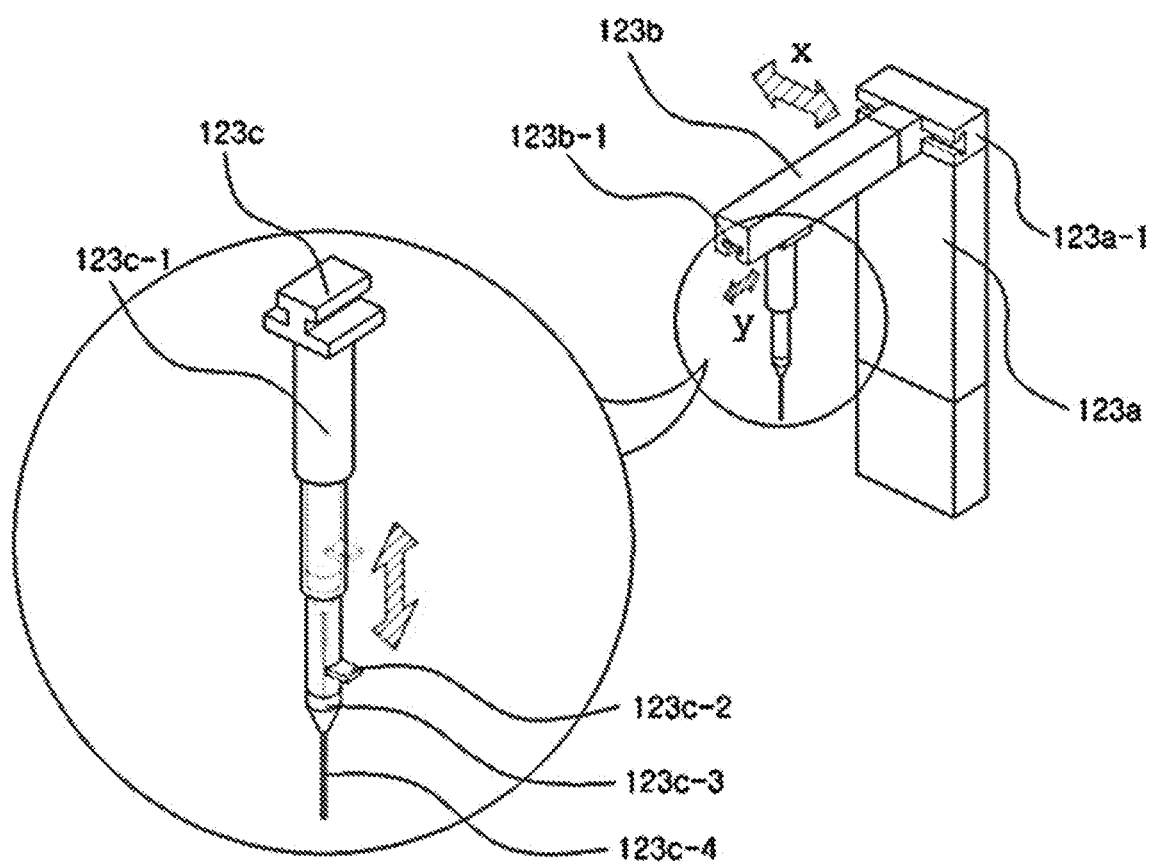
FIG. 5 is a perspective view of a skin hardness measuring unit according to some embodiments of the present invention.

As shown in FIG. 5, the skin hardness measuring unit 123 includes a hardness measuring support 123a, an x-axis moving bar 123b, and a y-axis moving unit 123c.

The hardness measuring support 123a is a rectangular plate shape formed upright on one side of the left side surface of the conveyor belt 110 in the traveling direction of the conveyor. An x-axis guide rail 123a-1 configured to be movable in the x direction, which is the conveyor traveling direction, is formed in the upper inner direction. This allows an x-axis moving bar 123b to reciprocate in the x direction within the range of the x-axis guide rail 123a-1.

The x-axis moving bar 123b is a straight bar formed perpendicular to the conveyor travel direction, is coupled to the x-axis guide rail 123a-1, and moves in the x direction which is the conveyor travel direction, and a y-axis guide rail 123b-1 which is movable in the y direction is formed on the bottom surface. Through this, the y-axis moving unit 123c is reciprocated in the y direction within the range of the y-axis guide rail 123b-1.

The y-axis moving unit 123c is inserted into the y-axis guide rail 123b-1 to form a hydraulic cylinder 123c-1 that moves in the y direction and moves up and down in the vertical lower direction, and a skin tissue sensor 123c-2 is formed on one side of a lower end of the hydraulic cylinder 123c-1, and a skin hardness measuring pin 123c-3 is formed on the lower end of the hydraulic cylinder 123c-1.

When the skin tissue sensor 123c-2 is located in front of the conveyor belt unit and when a skin tissue moving backwards is detected for the first time, the skin tissue sensor 123c-2 transmits the detection information to the follicle separation control unit 20 to stop the rotation of the conveyor belt 110. In addition, the hydraulic cylinder 123c-1 is moved down to measure the intensity of force of the skin hardness measurement pin 123c-3 piercing through the skin tissue to provide to the follicle separation control unit 20.

At this time, a pressure sensor is formed inside the skin hardness measurement pin 123c-3 to measure the pressure applied when the lower pin penetrates the skin tissue. The cutting force of the first cutting blade follicle separation control unit 134 and the second cutting blade follicle separation control unit 143 are set depending on the measured intensity of the pressure.

The lower pin 123c-4 is detachably coupled to the lower end of the skin hardness measuring pin 123c-3 to facilitate replacement and repair.

The first cutting unit 130 is positioned at a rear end of the scalp data analyzing unit 120 in the traveling direction of the conveyor belt to set the moving interval of the cutting blades according to the measured density from the scalp data, and cuts the scalp tissue into thin slices.

Figure 6:
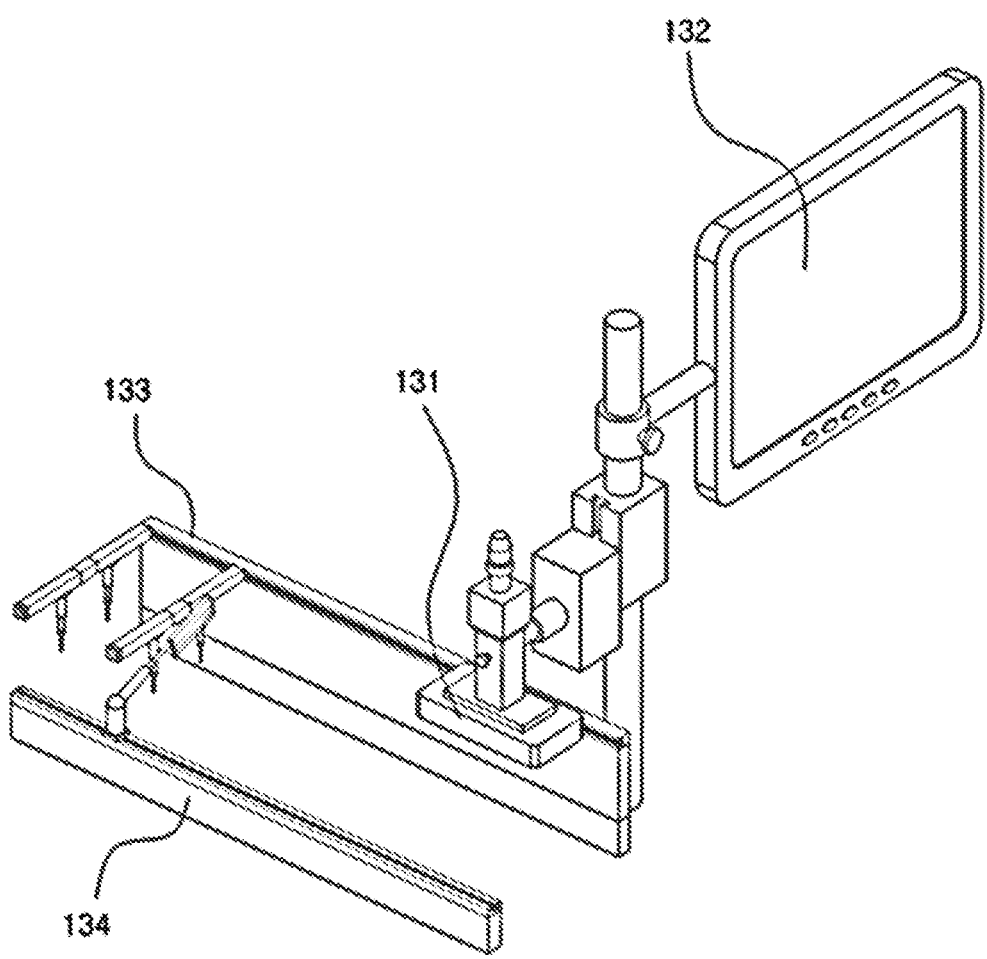
FIG. 6 is a perspective view of a first cutting unit according to some embodiments of the present invention.

As shown in FIG. 6, the first cutting unit 130 includes a first cutting scanning unit 131, a first monitor 132, a first pin fixing unit 133, and a first cutting blade follicle separation control unit 134.

The first cutting scanning unit 131 having a rectangular shape is positioned in a vertical direction on one side of an upper end of the conveyor belt, and moves up and down along the scanning guide rail formed in the vertical direction, scanning the front of the cut skin tissue to check the cutting position and recording an image of slicing the skin tissue in real time.

The first cutting scanning unit 131 scans the whole skin tissue by adjusting the focal length by moving up and down in the vertical direction according to the variable cutting position, and it is possible to zoom in/out of a portion to be scanned to provide a partially enlarged and reduced screen to the first monitor unit 132.

The first monitor unit 132 enlarges and displays the screen scanned by the first cutting scanning unit 131, so that a doctor can visually check the state of the front of the skin tissue and the screen information of being cut into slices.

The pin fixing unit 133 is supported on one side of the left side of the conveyor belt, and detects the position of the skin tissue identified by the scan in the first cutting scanning part, so that the vertical support pins located on the left and right sides of the front and rear are moved to the x and y directions. When the skin tissue is detected by the skin tissue sensor coupled to each vertical support pin which is moved in the axial direction, the pin fixing unit 133 moves down in the vertical direction to fix the skin tissue.

Figure 7:
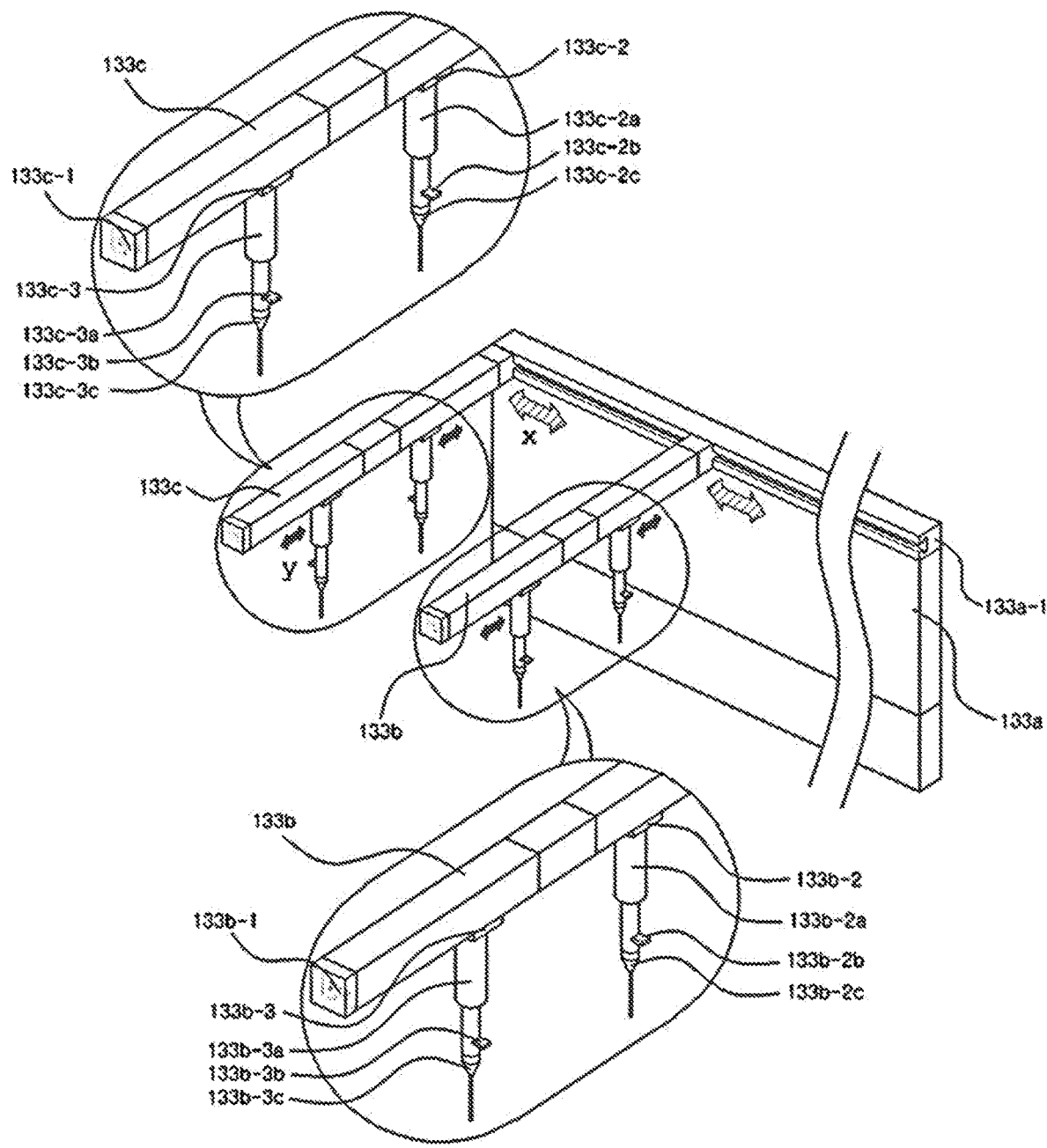
FIG. 7 is a perspective view of a pin fixing unit according to some embodiments of the present invention.

As shown in FIG. 7, the pin fixing unit 133 includes a pin fixing support 133a, a front pin fixing bar 133b, and a rear pin fixing bar 133c.

The pin fixing support 133a has a rectangular plate shape formed upright on one side of the left side surface of the conveyor belt 110 in the traveling direction of the conveyor. An x-axis guide rail 133a-1 movable in the x direction which is the traveling direction of the conveyor is formed in the upper inside direction. This allows the front pin fixing bar 133b and the rear pin fixing bar 133c to reciprocate in the x direction within the range of the x-axis guide rail 133a-1.

The front pin fixing bar 133b has a straight bar shape formed perpendicular to the conveyor traveling direction, is coupled to the x-axis guide rail 133a-1, and is moved in the x direction which is the conveyor traveling direction, and a y-axis guide rail 133b-1 is formed longitudinally at the bottom surface, and a front left pin support 133b-2 and a front right pin support 133b-3 are coupled to the y-axis guide rail.

The front left pin support 133b-2 has a hydraulic cylinder 133b-2a whose upper end is inserted into the y-axis guide rail 133b-1 and is moved in the y direction and moves up and down in the vertical lower direction. The skin tissue sensor 133b-2b is formed at one lower end of the hydraulic cylinder 133b-2a, and the front left pin 133b-2c is formed at the lower end of the hydraulic cylinder 133b-2a.

The front right pin support part 133b-3 has a hydraulic cylinder 133b-3a whose upper end is inserted into the y-axis guide rail 133b-1 and is moved in the y direction and moves up and down in the vertical lower direction. The skin tissue sensor 133b-3b is formed at one lower end of the hydraulic cylinder 133b-3a, and the front right pin 133b-3c is formed at the lower end of the hydraulic cylinder 133b-3a.

The rear pin fixing bar 133c is coupled to the x-axis guide rail 133a-1 in the shape of a straight bar formed perpendicularly to the conveyor traveling direction and moved in the x direction which is the conveyor traveling direction, and a y-axis guide rail 133c-1 is formed longitudinally at the bottom surface, and the rear left pin support 133c-2 and the rear right pin support 133c-3 are coupled to the y-axis guide rail.

The rear left pin support part 133c-2 has a hydraulic cylinder 133c-2a whose upper end is inserted into the y-axis guide rail 133c-1 and is moved in the y direction and moves up and down in the vertical lower direction. The skin tissue sensor 133c-2b is formed at one lower end of the cylinder 133c-2a, and a rear left pin 133c-2c is formed at the lower end of the hydraulic cylinder 133c-2a.

The rear right pin support part 133c-3 has a hydraulic cylinder 133c-3a whose upper end is inserted into the y-axis guide rail 133c-1 and is moved in the y direction and moves up and down in the vertical lower direction. The skin tissue sensor 133c-3b is formed at one lower end of the cylinder 133c-3a, and a rear right pin 133c-3c is formed at the lower end of the hydraulic cylinder 133c-3a.

According to some embodiments of the present invention, the front left pin 133b-2c and the front right pin 133b-3c are spaced apart from the rear of the first cutting blade follicle separation control unit 140 so that the front left and right sides of the skin tissue are pierced and supported in the vertical direction. The rear left pin 133c-2c and the rear right pin 133c-3c support and pierce the rear left and right sides of the skin tissue in the vertical direction, so that when the front side of the skin tissue is cut in a sliced form through the first cutting blade 134d-1, the skin tissue is prevented from being pushed and moved to another position, supporting stable cutting to be performed.

Also, according to some embodiments of the present invention, the front left pin 133b-2c is detachably screw-coupled to the lower end of the hydraulic cylinder 133b-2a, the front right pin 133b-3c to the lower end of the hydraulic cylinder 133b-2a, the rear left pin 133c-2c to the lower end of the hydraulic cylinder 133c-2a, and the rear right pin 133c-3c to the lower end of the hydraulic cylinder 133c-a, respectively, thereby facilitating replacement and repair.

This is to facilitate replacement when the pin is damaged during the cutting operation, and to replace the follicles after the separation of the follicles from the patient's connective tissue, thereby maintaining a clean sanitary condition at the time of follicle separation of the next patient.

The first cutting blade follicle separation control unit 134 is supported and positioned on one side of the right side of the conveyor belt, and a hydraulic cylinder having a blade fixed to the front perpendicularly to the conveyor belt travel direction is formed, rotates at a constant speed in the vertical direction, and descends. The skin tissue is cut into slices while reciprocating back and forth by a hydraulic cylinder.

Figure 8:
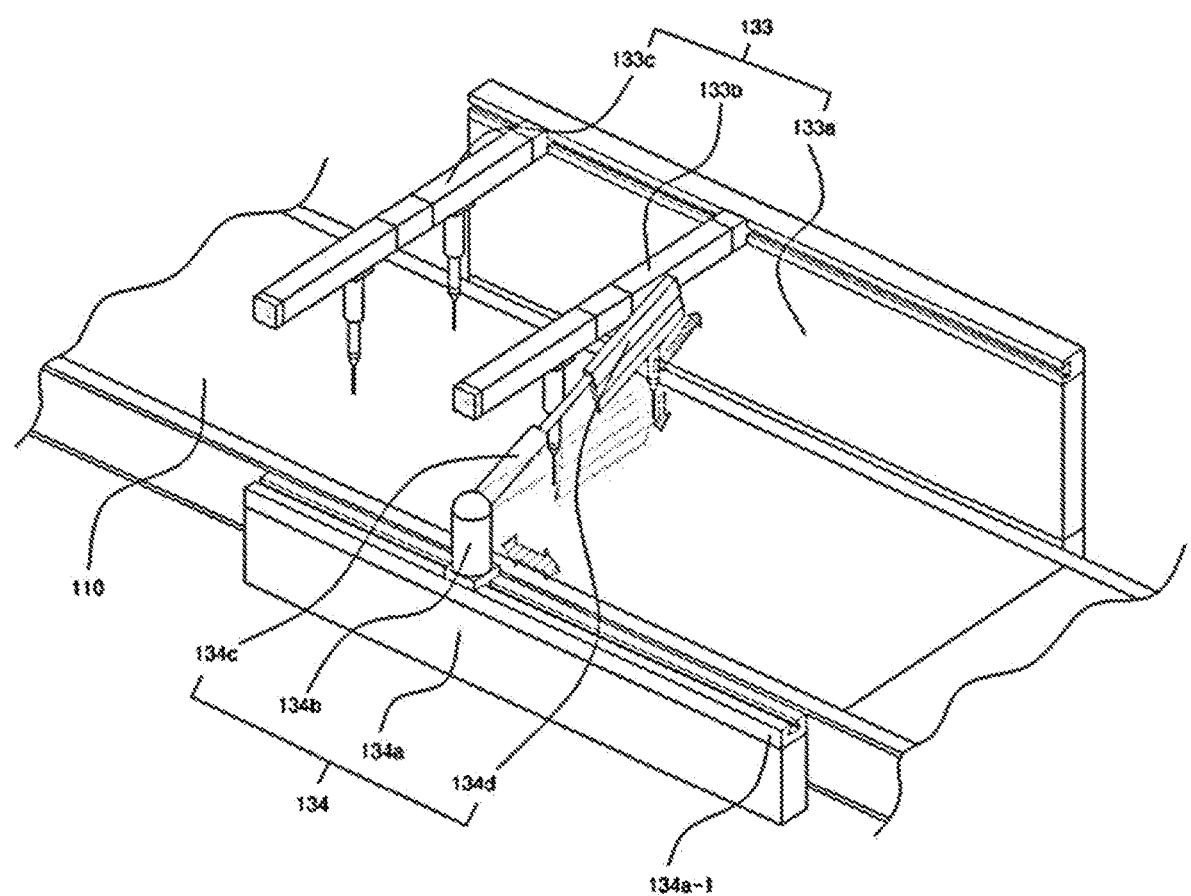
FIG. 8 is a perspective view of a first cutting unit according to some embodiments of the present invention.

As shown in FIG. 8, the first cutting blade follicle separation control unit 134 includes a first cutting blade support 134a, a first cutting rotary unit 134b, a first cutting hydraulic cylinder 134c, and a first cutting blade frame 134d.

The first cutting blade support 134a is a rectangular plate shape formed upright on one side of the right side surface of the conveyor belt 110 in the traveling direction of the conveyor. An x-axis guide rail 134a-1 movable in the x direction which is the traveling direction of the conveyor is formed in the upper inner direction. This allows the first cutting rotary unit 134b to reciprocate in the x direction within the range of the x-axis guide rail 134a-1.

The first cutting rotary unit 134b supports the first cutting hydraulic cylinder 134c perpendicularly to the conveyor traveling direction and moves in the x direction, and a rotating shaft is formed based on one side of the upper center to rotate the first cutting hydraulic cylinder 134c in an up-and-down direction.

Figure 9:
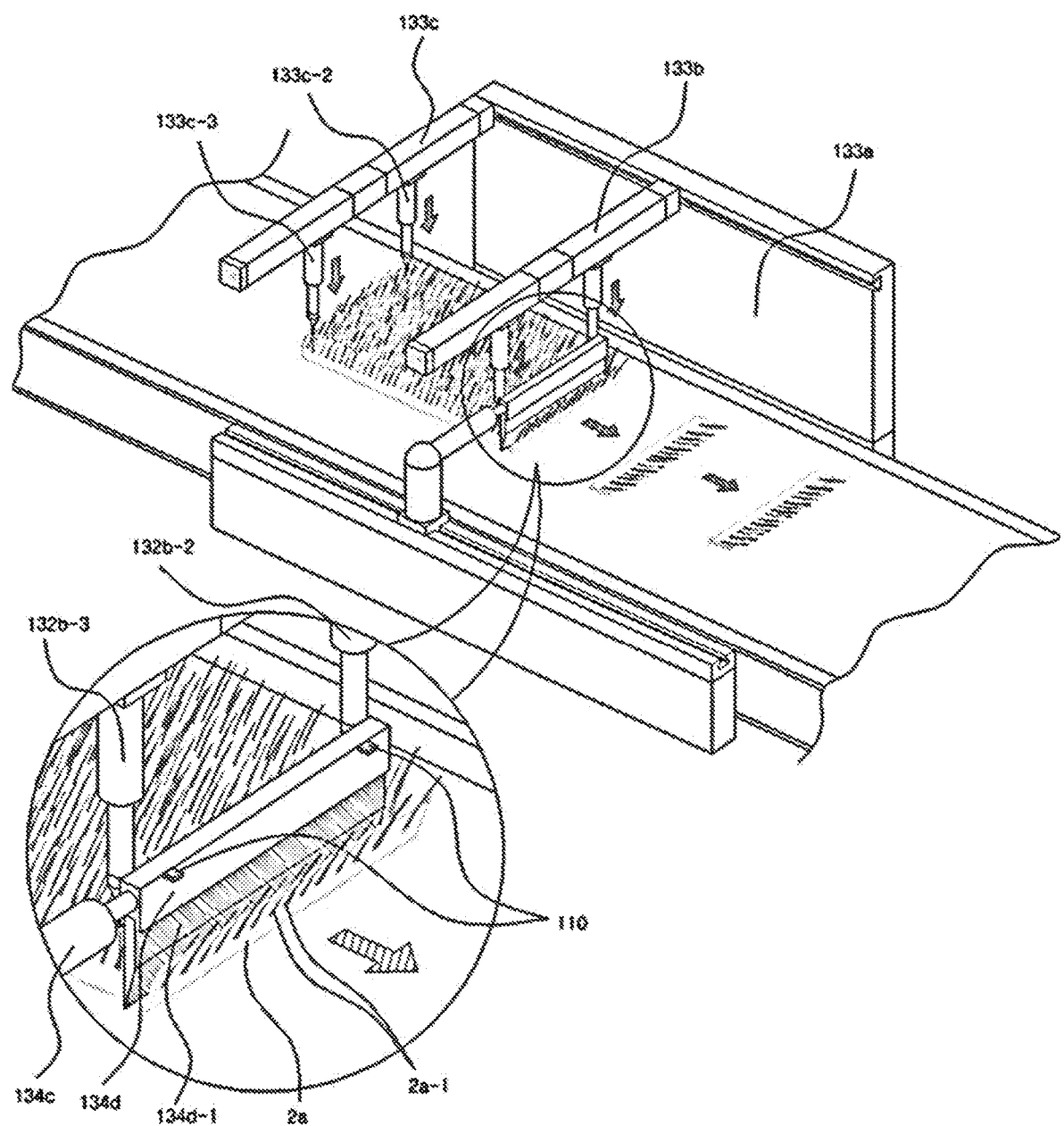
FIG. 9 is a perspective view of a pin fixing unit according to some embodiments of the present invention with a related enlarged diagram.

When the first cutting blade 134d-1 (see FIG. 9) cuts the skin tissue, the first cutting rotation part 134b slowly moves down within an angle range of 30° to −2°, and when the skin tissue is cut into slices, it moves up rapidly to prepare for the next process.

In a state where the first cutting blade 134d-1 is maintained at an angle of about 30° based on the first cutting rotary unit, when the skin tissue including a unit of follicles is located in the lower direction, the first cutting blade 134d-1 moves downward in the left and right directions, down to an angle of −2° to cut the skin tissue including the units of follicles in a slice form up to an upper side of the antibacterial cutting plate 111. This allows the skin tissue, including the units of follicles, to be completely cut into slices.

The first cutting hydraulic cylinder 134c is axially coupled perpendicularly to the upper inward direction of the first cutting rotary unit 134b and the first cutting blade frame 134d is coupled to the end of the cylinder to reciprocate the first cutting blade frame 134b through the reciprocation movement of the cylinder.

The first cutting hydraulic cylinder 134c reciprocates the first cutting blade frame 134d to stably cut the elastic skin tissue in a slice form.

The first cutting blade frame 134d is coupled to the end of the first cutting hydraulic cylinder 134c, and the first cutting blade 134d-1, which is easily coupled and detachably fitted in the lower direction, and a skin tissue sensor 134d-2 is formed at the front left and right sides.

Upon detection of the front part of the skin tissue positioned in a lower direction through skin tissue sensor 134d-2 formed at the front left and right sides, the first cutting blade frame 134d is lowered gradually in the vertical direction by the first cutting rotary unit 134b and reciprocated by the first cutting hydraulic cylinder 134c to cut the skin tissue into slices.

The second cutting unit 140 is formed upright in the rear end direction of the first cutting unit 130 to the left of the conveyor belt travel direction, the cutting blade is reciprocated in the vertical direction of the conveyor belt, and the each unit of follicles are individually separated by scanning each unit of follicles of the skin tissue cut into slices and cutting the left and right side portions respectively in the first cutting device.

According to some embodiments of the invention, the second cutting unit 140 further removes the tissue attached to the side portion of each incision of the units of follicles.

According to some embodiments of the present invention, the automatic hair-follicle separating apparatus 1 may further include a third cutting device unit (not shown) for removing tissue attached to the side portion of each unit of follicles cut between the second cutting unit 140 and the follicle selective unit 150.

Figure 10:
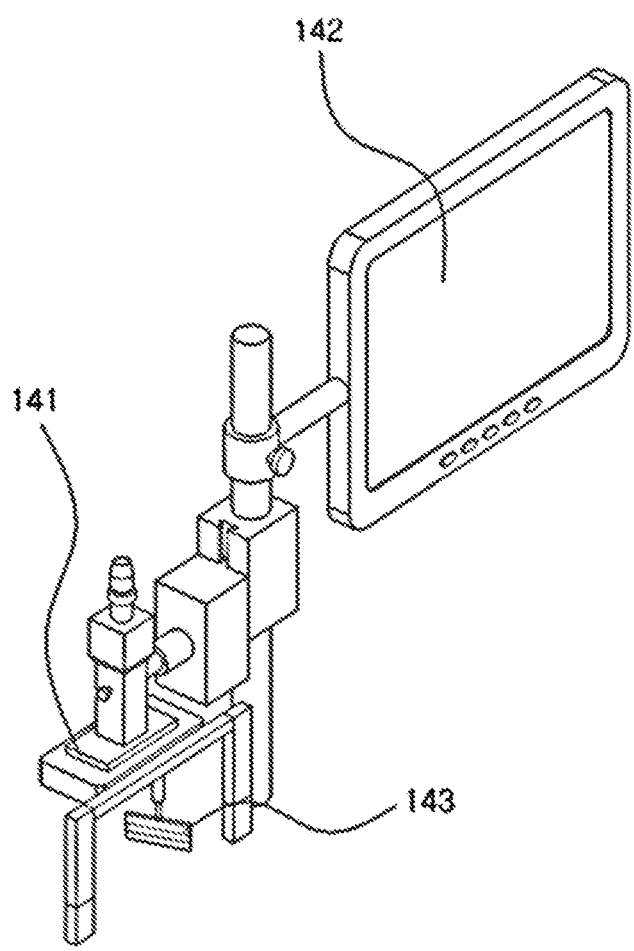
FIG. 10 is a perspective view of a second cutting unit according to some embodiments of the present invention.

As shown in FIG. 10, the second cutting unit 140 includes a second cutting scanning unit 141, a second monitor unit 142, and a second cutting blade follicle separation control unit 143.

The second cutting scanning unit 141 has a rectangular shape positioned in the center of one side of the upper end of the conveyor belt, and identifies the unit of follicles by scanning the connective tissue cut into slices by moving up and down along a scanning guide rail formed in a vertical direction. In addition, the position and direction information of the identified units of follicles is provided to the follicle separation control unit, and an image of scalp tissue being cut into slice shaped unit of follicles is taken in real time.

The second cutting scanning unit 141 moves up and down in the vertical direction and adjusts a focal length according to a variable cutting position to scan the connective tissue having a slice shape, and it is possible to zoom in/out of a portion to be scanned to provide a partially enlarged and reduced screen to the second monitor unit 142.

The second monitor unit 142 is located on the left side of the upright second cutting unit 140, and enlarges and displays the screen scanned by the second cutting scanning unit 141, so that a doctor can visually check the state of the slice shaped connective tissue and the screen information of cutting into units of follicles.

The second cutting blade follicle separation control unit 143 is a " ⊏ " shaped frame rotated 90 degrees clockwise (⊓) across the top of the conveyor belt, and the cutting blade reciprocates in the lower direction of the frame. The left and right sides of the units of follicles included in the sliced connective tissue are cut at regular intervals and separated into units of follicles individually.

Figure 11:
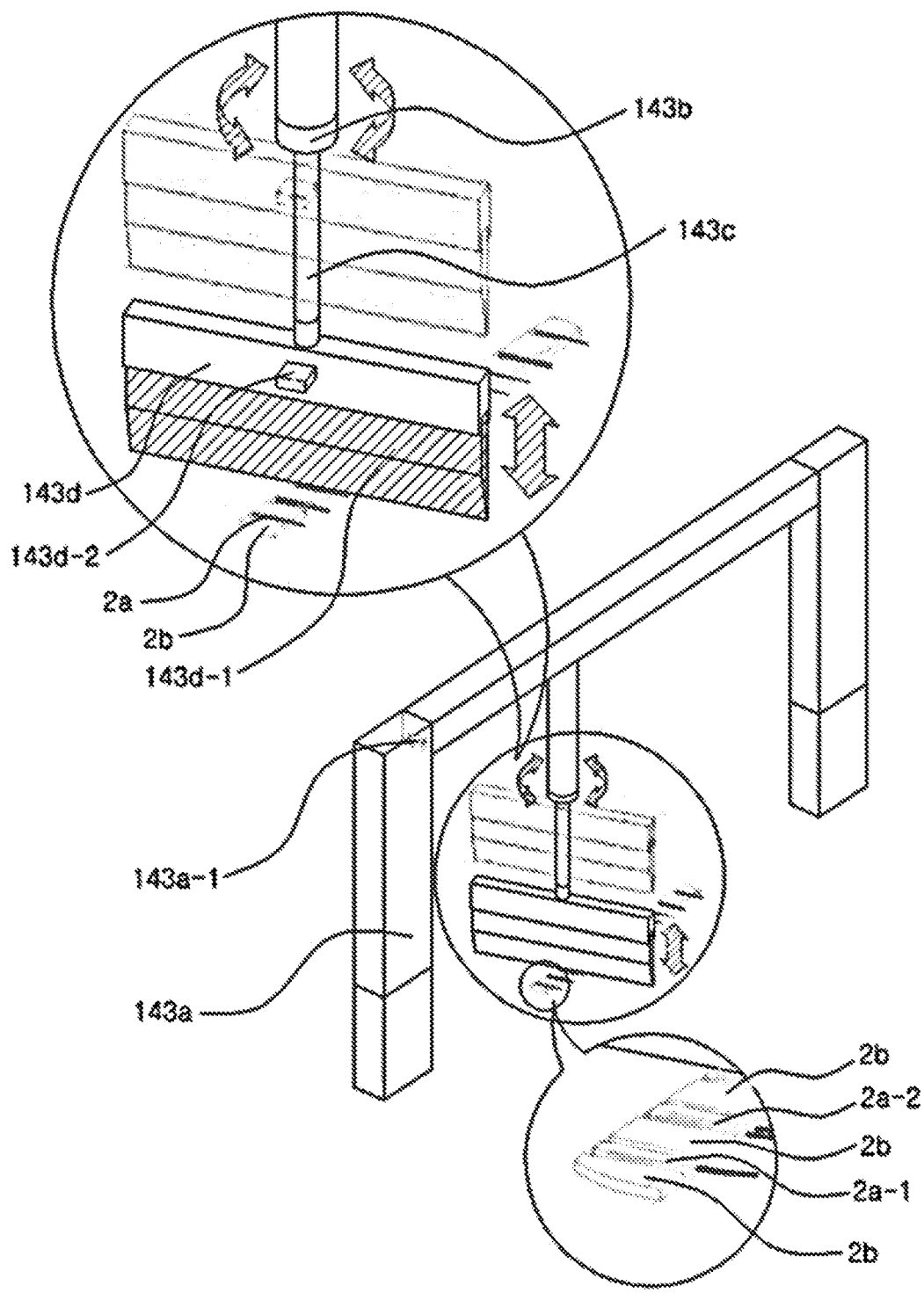
FIG. 11 is a perspective view showing a second cutting blade cutting a sliced connective tissue.

As shown in FIG. 11, the second cutting blade follicle separation control unit 143 includes a cutting blade support 143*a*, the second cutting rotary unit 143*b*, the second cutting hydraulic cylinder 143*c*, and the second cutting blade frame 1436*d*.

The cutting blade support 143*a* is a " ⊏ =" shaped frame rotated 90 degrees clockwise (⊓) across the top of the conveyor belt in the vertical direction, and a vertical guide rail 143*a*-1 is formed in the lower direction which reciprocates the second cutting rotary unit 143*b* in the vertical direction.

The second cutting rotary unit 143*b* has an upper end coupled to the vertical guide rail 143*a*-1 of the cutting blade support 143*a*, and rotates in a horizontal direction to form the second cutting hydraulic cylinder 143*c* and the second cutting blade frame 143*d*.

The second cutting rotary unit 143*b* receives the position and direction information of the follicles primarily through the second cutting scanning unit 141 and secondarily receives the position and direction information of the follicles through the follicle position sensor 143*d*-2. After receiving the information and moving to a position in the side vertical direction of the follicles, the second cutting rotary unit 143*b* rotates in the horizontal direction according to the direction of the follicles to set the position and direction for cutting only the left and right sides of the follicle in the slice shaped connective tissue.

Through this, regardless of the condition of the worker, the left and right sides of the slice-shaped connective tissue can be cut and separated without damage according to the direction of the follicles, thereby improving the engraftment rate of the follicles.

The second cutting hydraulic cylinder 143*c* has a cylinder shape coupled to the lower end of the second cutting rotary unit 143*b* and moves the second cutting edge frame positioned at the lower end while moving down and up in the vertical direction.

The second cutting blade frame 143*d* has a rectangular frame shape coupled to the lower end of the second cutting hydraulic cylinder 143*c*, and the second cutting blade 143*d*-1 is detachably coupled to the lower end by fitting. The follicle position sensor 143*d*-2 is configured to detect the position and the direction of the follicle in the lower direction in the center of the front upper side.

According to some embodiments of the present invention, the second cutting blades 143*d*-1 may be detachably coupled in a fitted manner to facilitate replacement. This is to maintain clean hygiene at the time of separation of the follicles of the next patient by replacing when the follicles are separated after the clean cutting is not made due to damage or wear of the cutting blade.

The follicle position sensor 143*d*-2 detects the position and direction of the follicles before the second cutting hydraulic cylinder moves down and sets the secondary position and rotation angle of the second cutting rotary unit, whereby the follicle damage can be minimized by the second cutting blade to maximize the engraftment rate of follicles.

Follicle selective unit 150 is cut in the form of follicles to the bottom of the frame of the " ⊏ =" shape rotated 90 degrees clockwise formed upright to the rear end direction of the second cutting unit 140 to the left of the conveyor belt travel direction. Each follicle is picked up, transported in a vertical direction, and selected and classified according to the number of hairs formed in the separated units of follicles.

Figure 12:
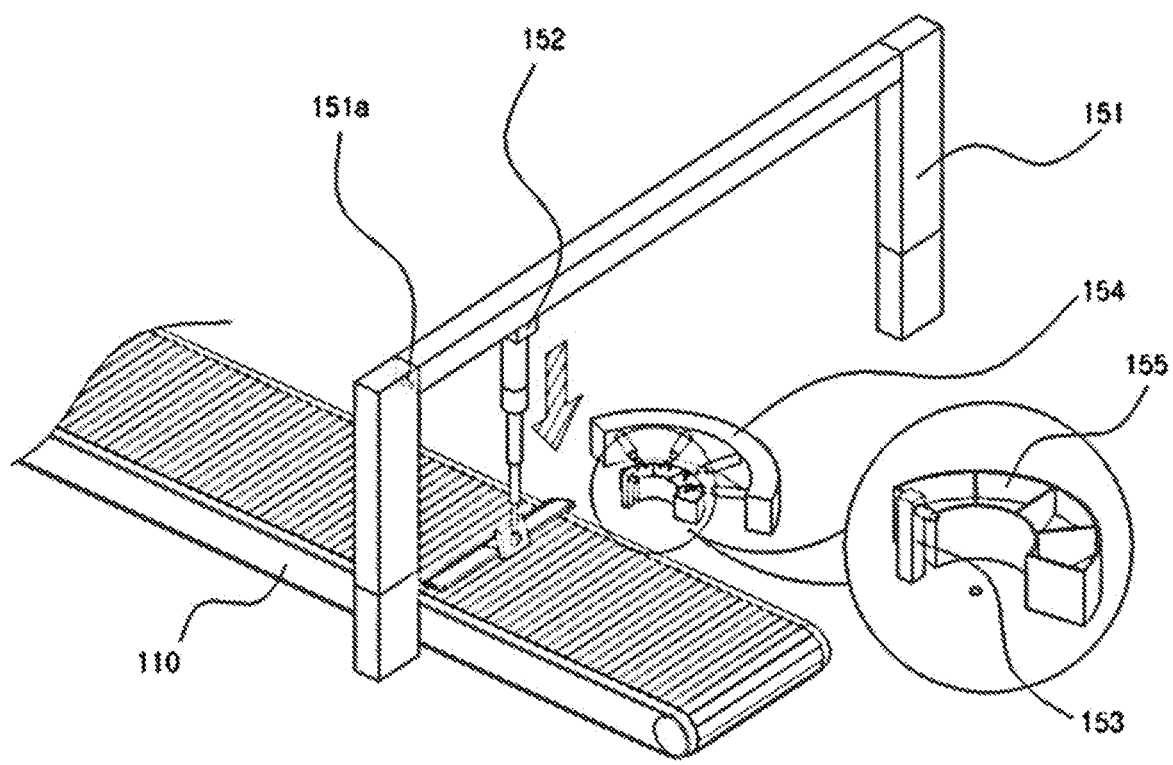
FIG. 12 is a perspective view of a follicle selecting unit according to some embodiments of the present invention.
Figure 13:
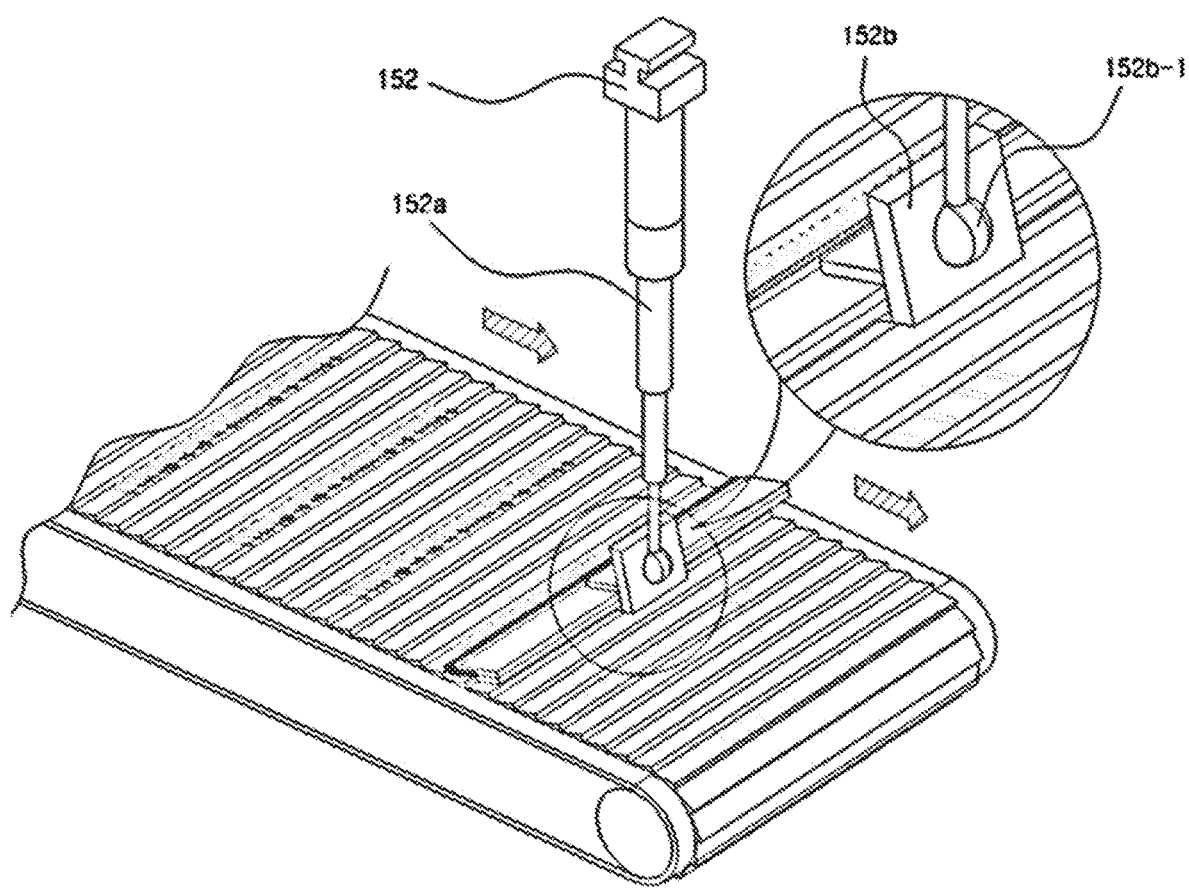
FIG. 13 is a perspective view of a selective follicle transporting unit according to some embodiments of the present invention.

As shown in FIG. 12, the follicle selective unit 150 includes a selective support 151, a follicle selective transporting unit 152, a follicle selective sensor 153, a follicle selective pincer 154, and a follicle storing unit 155.

The selective transporting support 151 is a " ⊏ =" shaped frame rotated 90 degrees clockwise across the top of the conveyor belt in a vertical direction, and a vertical guide rail 151*a* is formed to support a reciprocate vertically.

The follicle selective transporting unit 152 has a cylindrical shape coupled to the vertical guide rail 151*a* of the selective transporting support 151 at the top thereof, is reciprocated in the vertical direction and supports the follicle selective hydraulic cylinder 152*a* and the follicle selective transporting frame 152*b* coupled in the lower direction.

The follicle selective hydraulic cylinder 152*a* has a cylindrical shape coupled to the lower end of the follicle selective transporting unit 152, and the follicle selective transporting frame 152*b* is coupled to the lower end thereof, and the connective tissue in the form of slices cut in units of follicles is cut in the lower direction. The position of the follicle selective transporting frame 152*b* is controlled by moving up and down depending on whether it is the skin tissue is positioned.

The follicle selective transporting frame 152*b* has a semicircular vertical rotary unit 152*b*-1 shaft-coupled to the lower end of the follicle selective hydraulic cylinder 152*a*, and has a rectangular plate shaped frame formed in front of the vertical rotary unit, and a follicle bottom support frame 152*b*-2 and a follicle top support frame 152*b*-3 having the same length as the width of the conveyor belt in the front surface vertical direction of the frame.

Figure 15:
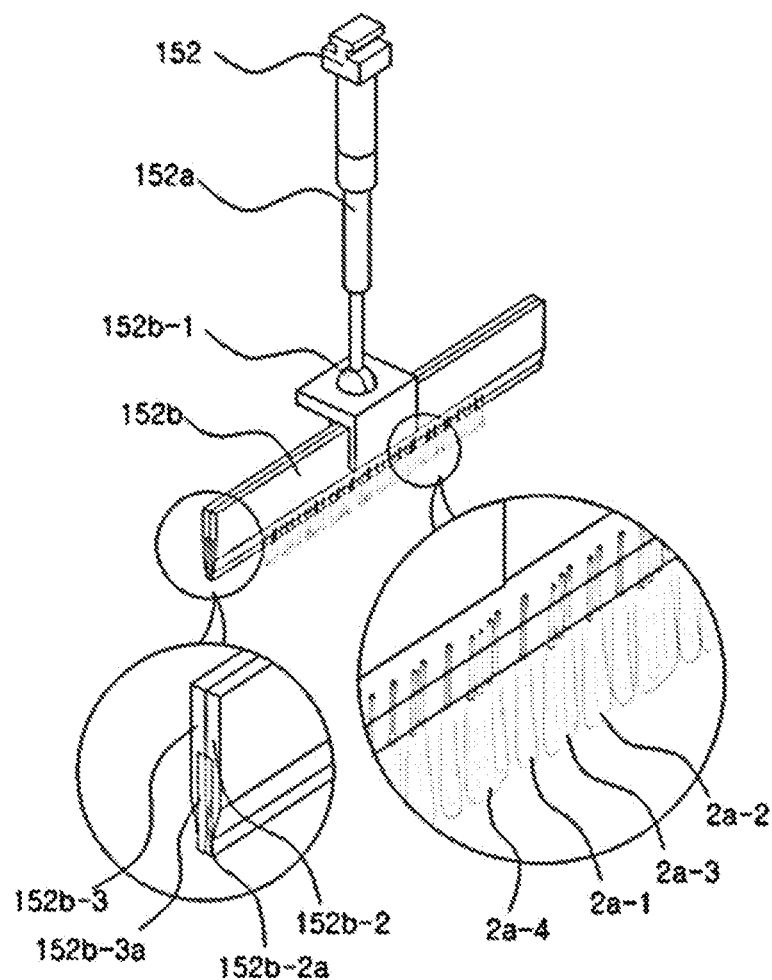
FIG. 15 is a perspective view of a selective follicle transporting unit according to some embodiments of the present invention.

At this time, the follicle bottom support frame 152*b*-2 is made of a support frame, as shown in FIG. 15, and the follicle top support frame 152*b*-3 is formed in a movable form capable of reciprocating in the vertical direction, and the follicle supporting top silicon 152*b*-3*a* is formed on the front lower surface in the longitudinal direction.

As shown in FIG. 15, the follicle bottom support frame 152*b*-2 is positioned at the bottom of the sawtooth pattern of the antibacterial cutting plate 111 of the conveyor belt so that when the hair of the separated follicles is placed on the follicle support bottom silicon 152*b*-2*a*, the follicle support top silicon 152*b*-3*a* is engaged with the follicle support bottom silicon 152*b*-2*a* with the follicle support bottom silicon 152*b*-2*a* lowered vertically to pick up hair separated in units of follicles positioned therebetween.

Thereafter, the follicle selective hydraulic cylinder 152*a* is raised, and the vertical rotary unit 152*b*-1 is rotated so that the follicle selective transporting unit 152 moves in the vertical direction along the vertical guide rail 151*a*.

The follicle support top silicon 152*b*-3*a* and the follicle support bottom silicon 152*b*-2*a* are made of a material having frictional force and elasticity and having antibacterial properties.

This prevents the hair of the separated unit of follicles from being exposed to bacteria or strongly picked up and damaged by bending, and prevents the hair from sliding down and falling down.

The follicle selective sensor 153 is formed so as to match the height of the units of follicles picked up during vertical movement of the follicle selective transporting unit, and detects the number of hairs formed in each of the separate units of follicles passing through the front direction to transport to the follicle separation control unit 20.

When the number of hairs formed in the unit of follicles passing through is one, the first follicle selective pincer 154*a* is moved and the hair is picked up so as to be stored in the first follicle storage groove 155*a*. When the number of hairs formed in the units of follicles passing through is two, the second follicle selective pincer 154*b* is moved and the hairs are picked up to be stored in the second follicle storage groove 155*b*. When the number of hairs formed in the units of follicles passing through is three, the third follicle selective pincer 154*c* is moved and the hairs are picked up to be stored in the third follicle storage groove 155*c*. When the number of hairs formed in the units of follicles passing through is four, the fourth follicle selective pincer 154*d* is moved and the hairs are picked up to be stored in the fourth follicle storage groove 155*d*.

This enables classification according to the number of hairs formed in the units of follicles to be provided to the doctor.

The follicle selective pincer 154 has a shape in which four pincers protrude from the inner surface of the semi-arc frame-shaped support at regular intervals on the inner side of the semi-arc frame-shaped support, which is picked up by the follicle selective transporting unit 152. The follicle selective pincer 154 is selected according to the number of hairs formed in the units of follicles passing through the follicle selective sensor.

Figure 16:
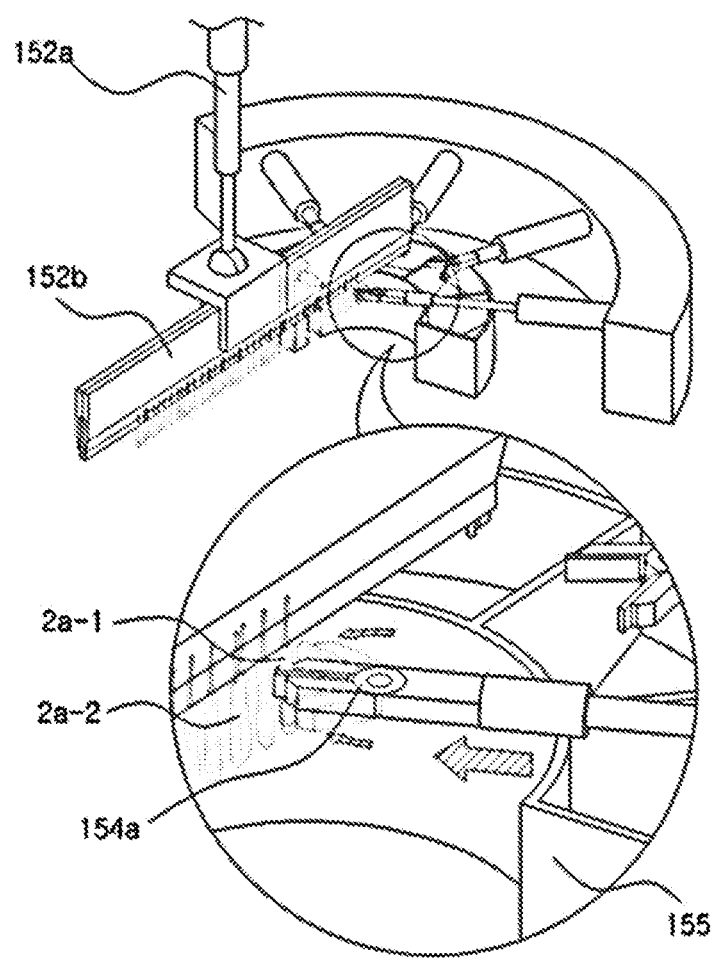
FIG. 16 is a perspective view of a selective follicle transporting unit and a selective follicle pincer according to some embodiments of the present invention.
Figure 17:
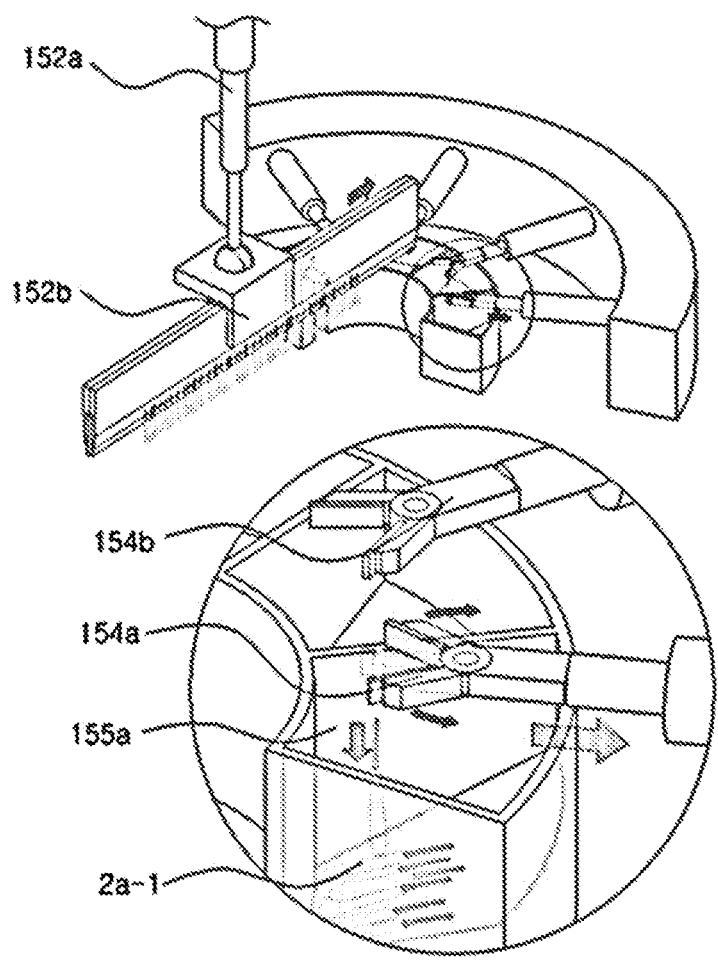
FIG. 17 is a perspective view of a selective follicle pincer and a first follicle storing unit according to some embodiments of the present invention.
Figure 18:
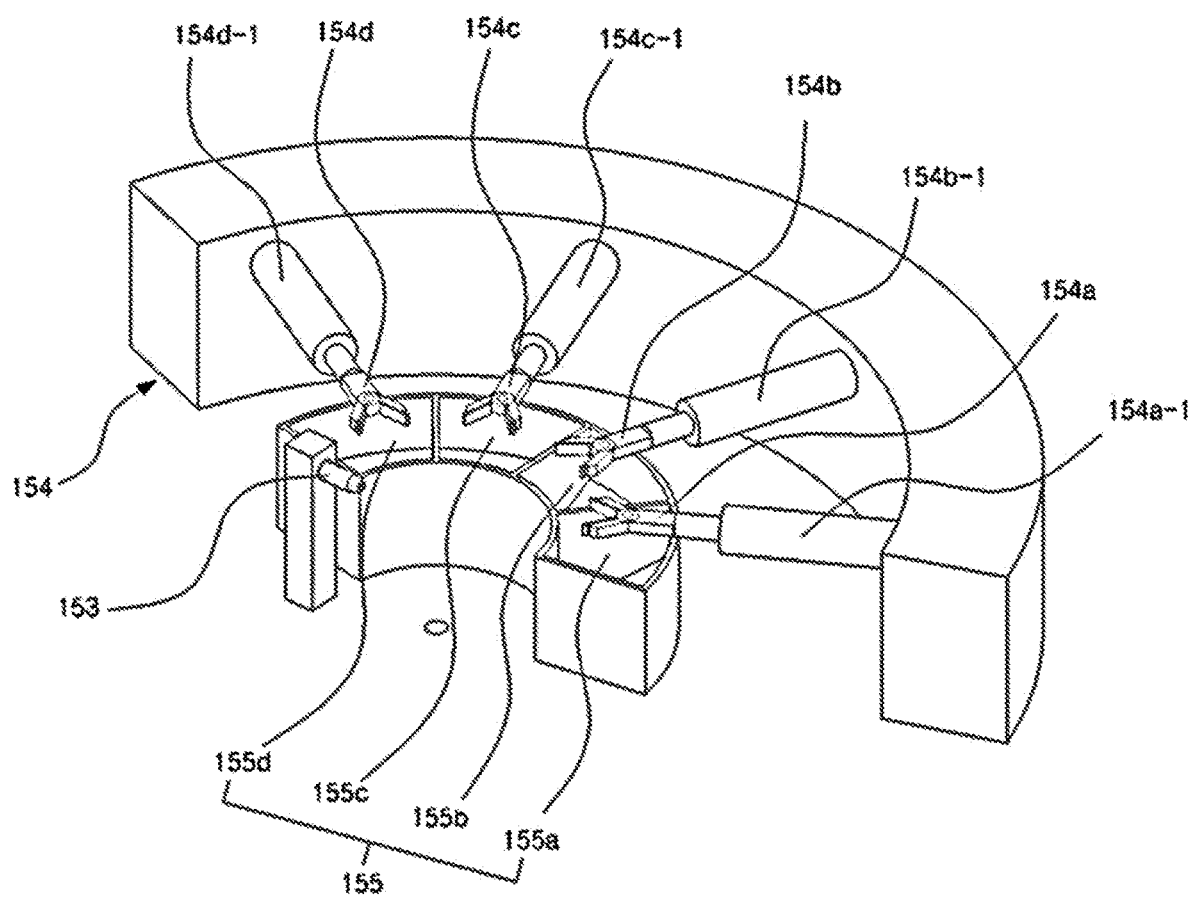
FIG. 18 is a perspective view of a selective follicle pincer and a first follicle storing unit according to some embodiments of the present invention.

As shown in FIGS. 16 and 17, the follicle selective pincer 154 includes a first selective follicle pincer 154*a*, a second follicle selective pincer 154*b*, a third follicle selective pincer 154*c*, and a fourth follicle selective pincer 154*d*.

First follicle selective pincer 154*a* is formed in the right direction with respect to the center point of the semi-arc support, the silicon material is coupled to the left and right sides of the front pincers of the pincers to have an structure that opens and closes according to rotation, and a first pincer hydraulic cylinder 154*a*-1 is formed at the rear of the pincers to reciprocate in the front-rear direction.

When the number of hairs formed in the unit of follicles passing through the front of the follicle selective sensor 153 is one, the first pincer hydraulic cylinder 154*a*-1 is moved forward, and a front pincer of the first follicle selective pincer 154*a* closes on a follicle formed having one hair positioned at the center of a semi-arc type support to pick up the hair and separate it from the follicle selective transporting unit, and then the first follicle selective pincer 154*a* returns to the rear and the front pincer opens for storing in the first follicle storage groove 155*a* positioned at the bottom.

The second follicle selective pincer 154*b* are formed on the left side of the first selective follicle pincer based on the center of the semi-arc support, and the silicon material is coupled to the left and right sides of the front pincer surface to open and close the pincer according to rotation. The second pincer hydraulic cylinder 154*b*-1 is formed at the rear of the pincer and reciprocates in the front-rear direction.

When the number of hairs formed in the units of follicles passing through the front of the follicle selection sensor 153 is two, the second pincer hydraulic cylinder 154*b*-1 is moved forward and a front pincer of the second follicle selective pincer 154*b* closes on a follicle formed having two hairs positioned at the center of a semi-arc type support to pick up the hair and separate it from the follicle selective transporting unit, and then the second follicle selective pincer 154*b* returns to the rear and the front pincer opens for storing in the second follicle storage groove 155*b* positioned at the bottom.

The third follicle selective pincer 154*c* are formed on the left side of the second selective follicle pincer based on the center point of the semi-arc support, and the silicon material is coupled to the left and right sides of the front pincers to open and close the pincers according to rotation. The third pincer hydraulic cylinder 154*c*-1 is formed at the rear of the pincer and reciprocates in the front-rear direction.

When the number of hairs formed in the units of follicles passing through the front of the follicle selective sensor 153 is three, the third pincer hydraulic cylinder 154*c*-1 is moved forward and a front pincer of the third follicle selective pincer 154*c* closes on a follicle formed having three hairs positioned at the center of a semi-arc type support to pick up the hair and separate it from the follicle selective transporting unit, and then the third follicle selective pincer 154*c* returns to the rear and the front pincer opens for storing in the third follicle storage groove 155*c* positioned at the bottom.

The fourth follicle selective pincer 154*d* is formed on the left side of the third selective follicle pincer based on the center point of the semi-arc support. The fourth pincer hydraulic cylinder 154*d*-1 is formed to the rear of the pincer and reciprocates in the front-rear direction.

When the number of hairs formed in the units of follicles passing through the front of the follicle selection sensor 153 is four, the fourth pincer hydraulic cylinder 154*d*-1 is moved forward and a front pincer of the fourth follicle selective pincer 154*d* closes on a follicle formed having four hairs positioned at the center of a semi-arc type support to pick up the hair and separate it from the follicle selective transporting unit, and then the fourth follicle selective pincer 154*c* returns to the rear and the front pincer opens for storing in the fourth follicle storage groove 155*d* positioned at the bottom.

The follicle storing unit 155 has a semi-arc frame shape formed inside the follicle selective pincer 154, and a storage groove is formed at the bottom of each pincers of the follicle selective pincers, and partition walls are formed at regular intervals between the pincers. An inclined surface is formed to an inner portion of each storage groove.

A first follicle storage groove 155*a* inclined to the inner portion at the bottom of the first selective follicle pincer 154*a* is formed, and a second follicle storage groove 155*b* inclined to the inner portion at the bottom of the second follicle selective pincer 154*b* is formed, a third follicle storage groove 155*c* inclined to the inner portion at the bottom of the third follicle selective pincer 154*c* is formed, and a fourth follicle storage groove 155*d* inclined to the inner portion at the bottom of the fourth follicle selective pincer 154*d* is formed.

The problem of a lowered engraftment rate can be prevented by laying down a gauze moistened with physiological saline and placing the separated follicles on the follicles when the separated follicles are dried or blown onto the saline at each follicle storage groove.

In addition, the bottom surface of each follicle storage groove is made of an inclined surface to prevent the mixed follicles falling to the bottom by the selective follicle pincers to be mixed irregularly and fall in a certain direction so that the doctor can use without a separate procedure for selecting follicles, thereby saving preparation time for surgery.

The non-incisional follicle separating unit 200 cuts and separates the connective tissue attached to the lateral part of the units of follicles, which is extracted directly from the back of the head of an alopecic patient, in units of follicles, and according to the number of hairs included in the units of follicles, the selecting is performed individually and the non-incisional follicle separating unit includes the conveyor belt 110, the first cutting unit 140, and the follicle selective unit 150.

The non-incisional follicle separating unit 200 positions the follicles and connective tissues extracted from the patient in one row at the rear end of the first cutting unit 130 in the advancing direction of the conveyor belt unit, and the second cutting unit 140 and the follicle selective unit 150 separates the hair follicle and the connective tissue in the same driving order as the incisional follicle separation device.

The non-incisional follicle separating unit 200 may be used in a state where the scalp data analyzing unit 120 and the first cutting unit 130 are turned off in the incisional follicle separating unit 100, or the scalp data analyzing unit 120 and the first cutting unit 130 may be removed so as to use the non-incisional follicle separating unit 200 in a compact form in which the length of the follicle separating unit 10 is reduced.

When using the scalp data analyzing unit 120 and the first cutting unit 130 in the OFF state, it is possible to use a combination of incisional follicle separation and non-incisional follicle separation.

When the scalp data analyzing unit 120 and the first cutting unit 130 are removed, the overall length of the non-incisional follicle separation device can be reduced, and the components of the device can be reduced to reduce the manufacturing cost of the device.

The follicle separation control unit 20 converts the scanned scalp image information and numerical values into data and displays them on the display of the monitor unit and controls operation by adjusting setting values such as reaction speed and moving speed of separation device.

Hereinafter, a description will be given of the specific operation process of the incision follicle separation unit in the automatic hair-follicle separating apparatus according to at least one embodiment of the present invention.

First, the scalp tissue extracted from the patient is placed in the center of the front upper part of the conveyor belt.

Next, the conveyor belt unit rotates and the scalp tissue is advanced, and when the conveyor belt unit is positioned at the lower end of the scanning unit, the rotation of the conveyor belt unit stops.

At this time, the skin hardness measurement pin of the skin hardness measurement unit moves to the x, y axis to position and then descends in the vertical direction to measure the scalp hardness by measuring the pressure passing through the scalp tissue.

Next, the conveyor belt unit rotates to position the scalp tissue at the lower end of the first cutting scanning unit, and then rotation is stopped. The front pin fixing bar and the rear pin fixing bar of the pin fixing unit are positioned at the front and the rear and then the front left and right pins, and the pin and the rear left and right pins descend to fix the scalp tissue.

Next, the first cutting blade support is located in front of the front pin fixing bar and the first cutting rotary unit is gradually rotated in the vertical lower direction, the first cutting hydraulic cylinder is reciprocated and the first cutting blade is moved to move forward one side of the skin tissue.

Next, the conveyor belt unit is rotated to position the connective tissue in the form of slice at the lower end of the second cutting scanning unit, and the rotation is stopped, and the follicle formed in the connective tissue in the form of slice is formed through the second cutting scanning unit and the follicle position sensor. After detecting the position and direction, the second cutting rotation part is rotated to position the second cutting blade in the lateral vertical direction of the follicle, and then lowered to cut the left and right sides of the follicle without damaging the follicle, thereby separating the connective tissue and each follicle.

Next, the conveyor belt unit is rotated to position the hair formed on the top of the follicles in the follicle support bottom silicon located in the follicle bottom support frame of the follicle selective transporting unit, and then the follicle support bottom silicon is lowered by lowering the follicle support bottom silicon. Then the separated follicles are placed in between and are moved up.

Next, the follicle selective transporting unit is stopped in front of the follicle selective sensor through a vertical guide rail, and at this time, the follicle selective pincers are selectively operated according to the number of hairs included in the follicles detected by the follicle selective sensor.

In this case, when the number of hairs contained in the follicles is one, the follicle selection first pincers are driven and inserted into the first follicle storage groove, and when the number of hairs included in the follicles is two, the follicles selection second pincers is driven and inserted into the second follicle storage groove. When the number of hairs inserted into the follicle storage groove, and the number of hair contained in the follicles is three, the follicle selection third pincers are driven and inserted into the third follicle storage groove, and when the number of hairs contained in the follicles is four, the follicle selection fourth pincers is driven and inserted into the fourth follicle storage groove.

Finally, by delivering undamaged healthy follicles selected and inserted into the follicle reservoir to the doctor for rapid hair transplantation, the engraftment rate of follicles planted in the scalp of the patient can be improved.

Hereinafter, a detailed operation process of the non-incisional follicle separation unit in the automatic hair-follicle separating apparatus according to at least one embodiment of the present invention will be described.

First, the connective tissue including the units of follicles pulled out directly from the back of the hair loss patient is placed in a single row so that the hair faces rearward in the center of the upper part of the conveyor belt of the front part of the second cutting device.

Next, when the connective tissue including the units of follicles arranged in a row at the bottom of the second cutting scanning unit is rotated by rotating the conveyor belt unit, the rotation is stopped, and the position of the follicle is detected through the second cutting scanning unit and the follicle position sensor. After detecting the direction, the second cutting rotary unit is rotated to position the second cutting blade in the lateral vertical direction of the follicles, and then descends to cut the left and right sides of the follicles without damaging the follicles to separate the connective tissue and each follicle.

Next, the conveyor belt unit is rotated to position the hair protruding in the upper direction of the follicles in the follicle support lower silicon located in the follicle bottom support frame of the follicle selective transporting unit, and then the follicle support lower silicon is lowered to support the follicle support lower silicon and the follicle support. Place separate follicles between the top silicon to be picked up and raise them.

Next, the follicle selective transporting unit is stopped by positioning the follicle selective sensor forward through the vertical guide rail, and at this time, selectively operates the follicle selective pincers according to the number of hairs included in the units of follicles detected by the follicle selective sensor.

In this case, when the number of hairs included in the units of follicles is one, the follicle selection first pincers are driven and inserted into the first follicle storage groove. When the number of hairs included in the units of follicles is two, the follicle selection second pincers are driven and inserted into the second follicle storage groove. When the number of hairs included in the units of follicles is three, the follicle selection third pincers are driven and inserted into the third follicle storage groove. When the number of hairs included in the units of follicles is four, the follicle selection fourth pincers are driven and inserted into the fourth follicle storage groove.

Finally, by delivering undamaged healthy follicles selected and inserted into the follicle storing unit to the doctor for rapid hair transplantation, the engraftment rate of follicles planted in the scalp of the patient can be improved.

In an embodiment of the present invention, various sensors such as a skin tissue sensor, a follicle position sensor, a follicle selective sensor may be used by selecting an appropriate type of sensor from among sensors such as an optical sensor and an ultrasonic sensor however it is not limited thereto.

In the embodiment of the present invention, a blade-type cutting blade is used for cutting blades such as the first cutting blade and the second cutting blade, but the present invention is not limited thereto. For example, skin tissue may be cut using a waterjet or a laser, if necessary.

At least one embodiment of the present invention uses a conveyor belt as a means for transporting skin tissue, but the present invention is not limited thereto. For example, the sample plate may be moved in the front-rear direction by converting the rotational motion of the drive motor into a linear motion using a sample plate for placing skin tissue and a rack and pinion device.

In the embodiment of the present invention, the pin is moved up and down by using a hydraulic cylinder to the pin fixing portion for fixing the skin tissue on the conveyor belt, but the present invention is not limited thereto. For example, a pin or a solenoid device may be used to move the pin up and down as needed.

According to some embodiments of the present invention, coupling schemes such as fit coupling or screw coupling may be interchanged as necessary, and the fitting coupling may include a click structure.

As described above, according to some embodiments of the present invention, when classifying follicles by a number of hairs included in each follicle by separating the follicles from a skin tissue cut out from a certain part of a scalp of an alopecic patient in an incisional hair transplant, or classifying follicles by a number of hairs included in each follicle directly extracted from the back of the head of the alopecic patient in a non-incisional hair transplant, it is possible to minimize the loss of healthy follicles regardless of the skill and fatigue level of a worker, to automatically make selections depending on the number of hairs formed in each separated follicle to save operation time and thereby relieving the physical stress on doctors and patients, to separate the follicles at a high speed so that the follicles are quickly delivered in an undried state to increase the engraftment rate of transplanted hair, and to automatically separate follicles without the need for follicle separating professionals to reduce labor costs and thereby ultimately reducing the cost of surgery for patients to generalize hair transplant surgeries.

The present disclosure should not be limited to these embodiments but various changes and modifications are made by one ordinarily skilled in the art within the subject matter, the spirit and scope of the present disclosure as hereinafter claimed. Specific terms used in this disclosure and drawings are used for illustrative purposes and not to be considered as limitations of the present disclosure. Exemplary embodiments of the present disclosure have been described for the sake of brevity and clarity. Accordingly, one of ordinary skill would understand the scope of the claimed invention is not to be limited by the explicitly described above embodiments but by the claims and equivalents thereof.

What is claimed is:

1. An apparatus for automatically separating hair follicles, the apparatus comprising:
   a follicle separating device configured to cut a skin tissue of a scalp cut from a back of a head of an alopecic patient in units of follicles and to classify follicles by a number of hairs included in each follicle in an incisional hair transplant; and
   a follicle separation controller configured to control an operation of the follicle separating device, wherein
   the follicle separating device includes
      a transporting member configured to transport the skin tissue or the follicles by a rotation of a driving motor controlled by the follicle separation controller,
      a scalp data analyzer configured to scan the skin tissue, to measure a density of hairs on the scalp, and to measure hardness of the skin tissue,
      a first cutting member including a first cutting blade, positioned at a subsequent stage of the scalp data analyzer in a moving direction of the transporting member, and configured to set a moving interval of the first cutting blade based on measured density of hairs and to cut the skin tissue in a slicing manner,
      a second cutting member including a second cutting blade configured to make a reciprocating movement in a direction perpendicular to the transporting member, positioned in a standing form at a subsequent stage of the first cutting member on a first side in the moving direction of the transporting member, and configured to scan the skin tissue sliced by the first cutting member and to separate each follicle by cutting side portions of each follicle, and
      a follicle selector configured to classify the follicles cut by the second cutting member based on the number of hairs included in each follicle.

2. The apparatus according to claim 1, further comprising a first monitor including a first display, wherein, in the incisional hair transplant,
   the follicle separating device is configured to collect information and figures on a scalp image obtained by scanning the scalp,
   the follicle separation controller is configured to perform a datafication of the information and figures on the scalp image collected by the follicle separating device and to output dataficated information and figures on the scalp image to the first monitor, and
   the first monitor is configured to display the dataficated information and figures on the scalp image outputted from the follicle separation controller on the first display.

3. The apparatus according to claim 1, wherein the scalp data analyzer includes
   a scanner configured to move up and down along a scanning guide rail formed in an up-and-down direction, to determine a follicle distribution by scanning a whole skin tissue, and to measure an average density of follicles in the skin tissue by measuring an interval between follicles, a skin hardness measuring member including a skin hardness measuring pin moving in x and y directions and a skin tissue sensor and configured to measure an intensity of force of the skin hardness measuring pin piercing through the skin tissue, and a first monitor including a first display, and configured to display a screen scanned by the scanner in a magnified manner and information obtained by the skin hardness measuring member on the first display.

4. The apparatus according to claim 1, wherein the first cutting member includes a first cutting scanner having a rectangular shape positioned on one side above the transporting member and configured to move up and down along a scanning guide rail formed in an up-and-down direction, to check a cutting point by scanning a leading portion of the skin tissue, and to record an image of slicing the skin tissue in real time, a second monitor including a second display and configured to display a screen scanned by the first cutting scanner in a magnified manner on the second display, a pin fixing member positioned on one side above the transporting member, including a plurality of pins moving in x and y directions and configured, when the skin tissue is detected, to move down to fix the skin tissue, and a first cutting blade controller positioned on one side above the transporting member, including a hydraulic cylinder with the first cutting blade, and configured to slice the skin tissue by a reciprocating movement of the hydraulic cylinder.

5. The apparatus according to claim 1, wherein the second cutting member includes a second cutting scanner having a rectangular shape positioned on one side above the transporting member and configured to move up and down along a scanning guide rail formed in an up-and-down direction, to identify each follicle by scanning a sliced skin tissue, to provide information on position and direction of each identified follicle to the follicle separation controller, and to record an image of dicing each follicle in real time, a second monitor including a second display and configured to display a screen scanned by the second cutting scanner in a magnified manner on the second display, and a second cutting blade controller including a frame traversing above the transporting member and the second cutting blade moving in an up-and-down direction and configured to separate each follicle by cutting both sides of each follicle from the sliced skin tissue.

6. The apparatus according to claim 1, further comprising an antibacterial cutting plate including a belt having a side cross section formed in a sawtooth shape with a slope heading a rear upper direction and formed of an antibacterial and corrosion-resistant material, wherein the antibacterial cutting plate is configured to be attached on the transporting member.

7. The apparatus according to claim 1, wherein the transporting member includes a conveyor belt formed from a leading end to a trailing end of the transporting member and configured to move in a linear direction by a rotation of a driving motor.

\* \* \* \* \*